(12) United States Patent
Laufer et al.

(10) Patent No.: US 9,181,394 B2
(45) Date of Patent: Nov. 10, 2015

(54) COMPOSITION FOR PRODUCING CAST POLYAMIDES

(75) Inventors: Wilhelm Laufer, Ellerstadt (DE); Benjamin Bechem, Mannheim (DE); Andre Palzer, Bruhl (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 14/122,110

(22) PCT Filed: May 23, 2012

(86) PCT No.: PCT/EP2012/059619
§ 371 (c)(1),
(2), (4) Date: Jan. 30, 2014

(87) PCT Pub. No.: WO2012/163764
PCT Pub. Date: Dec. 6, 2012

(65) Prior Publication Data
US 2014/0148570 A1      May 29, 2014

(30) Foreign Application Priority Data
May 30, 2011 (EP) .................................... 11168080

(51) Int. Cl.
*C08G 69/16* (2006.01)
*C08G 69/18* (2006.01)
*C07D 223/10* (2006.01)

(52) U.S. Cl.
CPC .............. *C08G 69/18* (2013.01); *C07D 223/10* (2013.01); *C08G 69/16* (2013.01)

(58) Field of Classification Search
None
See application file for complete search history.

(56) References Cited

U.S. PATENT DOCUMENTS 5,264,479 A    11/1993   Heinz et al.

FOREIGN PATENT DOCUMENTS

DE       3007118      *   9/1981

OTHER PUBLICATIONS

Machine translation of DE 3007118.*
International Search Report from International Application PCT/EP2013/059619 dated Aug. 20, 2009, 2 pages.

* cited by examiner

*Primary Examiner* — Ana Woodward

(57) ABSTRACT

The present invention relates to novel compositions for producing cast polyamides.

12 Claims, No Drawings

COMPOSITION FOR PRODUCING CAST POLYAMIDES

The present invention relates to novel compositions for producing cast polyamides.

Cast polyamides are polyamides of particularly high molecular weight. In the production of cast polyamides, a lactam is cast together with at least one catalyst and at least one activator into a mold and is then polymerized anionically in said mold. The starting compounds present in the mold here generally polymerize with exposure to heat. This process gives a homogeneous material which is superior to extruded polyamides in terms of crystallinity.

Cast polyamides are suitable thermoplastics for the manufacture of complex components. Unlike many other thermoplastics, they do not have to be melted, but instead are produced through anionic polymerization of a lactam in a mold at from 120 to 160° C. at atmospheric pressure, in just a few minutes. Any of the known casting processes can be used here, for example ingot casting, rotomolding, and centrifugal casting. The final product obtained in each case comprises moldings made of a high-molecular-weight, crystalline polyamide and featuring low weight, high mechanical strength, very good slip properties, and excellent chemicals resistance, and—since materials are not charged under pressure to the molds—with only low levels of internal stress. Cast polyamides can be sawn, drilled, milled, ground, abraded, and printed or coated; this polymer is used not only for manufacture of complex hollow shapes but also by way of example for manufacture of pulleys for passenger elevators, and semifinished products such as pipes, rods, and sheets for mechanical engineering and the automobile industry.

It is known per se that cast polyamide parts can be produced by what is known as activated anionic polymerization from low-viscosity lactam melts and a catalyst, and also an activator. This is usually achieved by producing, separately from one another, two mixtures of catalyst and lactam and, respectively, activator and lactam, in the form of a fresh liquid melt prior to the polymerization process, immediately mixing these with one another, and then polymerizing the mixture in the casting mold. This method is intended to ensure that no undesired premature reaction occurs.

Disadvantages of the compositions known in the prior art are that these either include solid activators with low activity or include solvent-containing liquid polyisocyanates.

It is therefore an object of the present invention to provide compositions which do not have the disadvantages of the prior art.

Surprisingly, it has now been found that compositions comprising
a) at least one lactam and
b) at least one activator for the anionic polymerization of lactams of the formula (I)

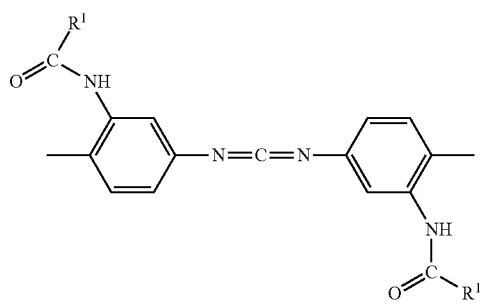

where $R^1$=lactam, preferably caprolactam, do not have the disadvantages of the prior art.

The present invention therefore provides compositions comprising
a) at least one lactam and
b) at least one activator for the anionic polymerization of lactams, where the activator involves a compound of the formula (I)

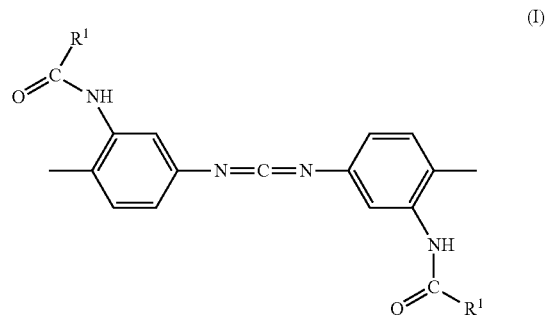

where $R^1$=lactam, preferably caprolactam.

In another preferred embodiment of the invention, the activator involves a compound of the formula (II)

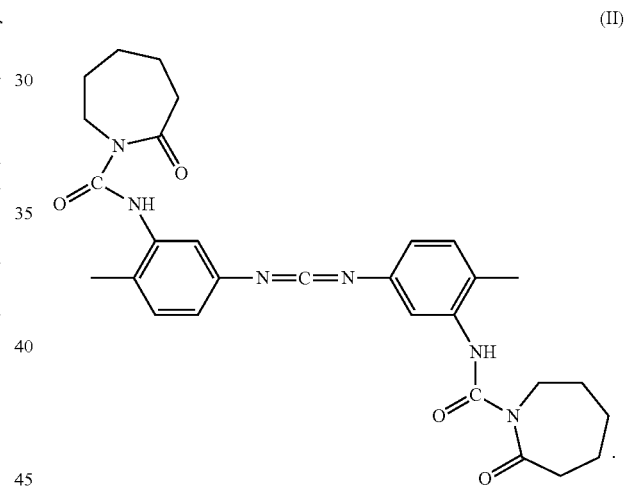

The activators preferably involve compounds which are obtainable through reaction of N,N'-bis(3-isocyanato-4-methylphenyl)carbodiimide with caprolactam in the process familiar to the person skilled in the art.

The production process preferably takes place in the presence of a solvent, e.g. petroleum spirit or alkylbenzenes, e.g. toluene or xylene.

Compounds of the general formula (III)

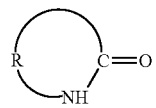

can be used as lactam for the purposes of the invention, where R is an alkylene group having from 3 to 13 carbon atoms. It is preferable that caprolactam and/or laurolactam is involved here. These are available commercially, e.g. from Lanxess Deutschland GmbH.

The abovementioned compounds are available commercially and by way of example are obtainable from Rhein Chemie Rheinau GmbH or from Bayer MaterialScience AG.

In another embodiment of the invention, the composition also comprises at least one catalyst selected from the group of lactam magnesium halide, alkali metal aluminodilactamate, alkali metal lactamate, and/or alkaline earth metal lactamate. Sodium caprolactamate is particularly preferred here.

The abovementioned catalysts are available commercially and by way of example are obtainable from Rhein Chemie Rheinau GmbH or from KatChem spol.s.r.o.

In another embodiment of the invention, the composition has the following proportions of a) to c):
a) from 94 to 99.9% of at least one lactam,
b) from 0.1 to 5%, preferably from 0.2 to 2%, particularly preferably from 0.2 to 0.8%, of at least one activator, and
c) from 0 to 5% of at least one catalyst,
where the entirety of the constituents is 100%.

The percentage data involve % by weight.

In another embodiment of the invention, the composition of the invention also comprises other additives, such as impact modifiers, e.g. polyetheramine copolymers, continuous-filament or other glass fibers, carbon fibers, aramid fibers, and/or processing aids, for example high-molecular-weight polyols, thickeners, e.g. Aerosil products, UV stabilizers and heat stabilizers, conductivity improvers, for example carbon blacks and graphites, ionic liquids, marking substances, and/or colors.

The present inventions moreover provide a process for producing cast polyamides which constituents a) and b) and optionally c) of the composition of the invention in the form of melt are polymerized at temperatures of from 80 to 160° C.

In the cases where the composition of the invention also comprises other additives, these can be added prior to and/or during the polymerization process.

The amount of additives is determined by the intended use and can therefore be varied as desired.

Polymerization is achieved by the processes familiar to the person skilled in the art, for example as described in Kunststoffhandbuch [Plastics Handbook], vol. 3/4, Technische Thermoplaste [Engineering Thermoplastics], Hanser Fachbuch, pp. 413-430. The mixture here is preferably stirred. Mixing assemblies can be used for this purpose, examples being stirred tanks.

The present invention further provides the use of the composition of the invention for producing cast polyamides.

The abovementioned compositions of the invention are preferably used as replacement for metal, e.g. in the automobile industry, in the production of electrical-engineering parts, and for electronic applications, for the production of sheets, bars, pipes, cable pulleys, gearwheels, and bearings, and/or for the manufacture of containers.

The scope of the invention encompasses, in combination with one another, all of the moiety definitions, indices, parameters, and explanations mentioned above and listed hereinafter or mentioned in preferred ranges, i.e. also encompasses any desired combination involving the respective ranges and preferred ranges.

The examples below serve for explanation of the invention, without any resultant limiting effect.

INVENTIVE EXAMPLES

Reagents

Anhydrous caprolactam (FP>69° C.) from Lanxess Deutschland GmbH.

Catalyst used comprises: Addonyl® Kat NL from Rhein Chemie Rheinau GmbH, about 18% of sodium caprolactamate in caprolactam.

Activators used comprise:
1) Caprolactam-blocked N,N'-bis(3-isocyanato-4-methylphenyl)carbodiimide of formula (II) (of the invention), see example 1,
2) Addonyl® 8108: aliphatic polyisocyanate solution, obtainable commercially from Rhein Chemie Rheinau GmbH, see example 2,
3) Brüggolen® C20 P: caprolactam-blocked hexamethylene diisocyanate in caprolactam, obtainable commercially from Brüggemann GmbH, see example 3,
4) N,N'-bis(3-isocyanato-4-methylphenyl)carbodiimide: monomeric carbodiimide based on tolylene 2,4-diisocyanate, see example 4,
5) Stabaxol® P: aromatic polycarbodiimide based on 1,3,5-triisopropyl-2,4-diisocyanato-benzene, see example 5,
6) Addolink® TT: dimeric TDI uretdione, see example 6.

Equipment

The apparatus used for melt preparation was composed of:
2 three-necked flasks (500 ml) heated in an oil bath
2 precision-glass-gland stirrers with sleeve
2 gas caps, 1 with valve and 1 without valve
1 vacuum pump with cold trap and manometer.

The apparatus used for temperature measurement was composed of:
temperature measurement device, e.g. Testo 175-T3 with IR serial interface
thermocouple wire to remain in the hardened specimen
600 ml glass beaker (tall shape) and
heating system for the glass beaker (metal block, oil bath).

Method and Assessment 196.8 g of caprolactam and activator were charged to flask A, and 192 g of caprolactam and 8 g of NL-Neu catalyst were charged to flask B.

The melts from flasks A and B were prepared in vacuo (<15 mbar) at 122° C. (±2° C.) in an oil bath for 20 minutes.

Nitrogen was introduced, and then components from flask A and flask B were combined into a three-necked flask, briefly stirred, and transferred to the 600 ml glass beaker.

The temperature of the mold (glass beaker) was 160° C. The polymerization time was generally from 10 to 20 minutes.

TABLE 1 shows the results.

| Activator | Example 1 (inv.) | Example 2 (comp.) | Example 3 (comp.) | Example 4 (comp.) | Example 5 (comp.) | Example 6 (comp.) |
|---|---|---|---|---|---|---|
| 0.8% by wt. | Cast PA* | Cast PA | Cast PA | No cast PA | Cast PA | Cast PA |
| 0.5% by wt. | Cast PA | Cast PA | Cast PA | | No cast PA | No cast PA |

TABLE 1-continued shows the results.

| Activator | Example 1 (inv.) | Example 2 (comp.) | Example 3 (comp.) | Example 4 (comp.) | Example 5 (comp.) | Example 6 (comp.) |
|---|---|---|---|---|---|---|
| 0.3% by wt. | Cast PA | Cast PA | No cast PA | | | |
| 0.2% by wt. | Cast PA | Cast PA | | | | |
| 0.1% by wt. | No cast PA** | No cast PA | | | | |

*Production of cast polyamide parts successful
**No or incomplete polymerization The examples show that the composition of the invention permits production of cast polyamide parts even at very low activator concentrations. The only way of achieving similarly good results is to use polyisocyanate solutions as activator component. However, these have the disadvantage that they contain solvent.

What is claimed is:

1. A composition comprising:
   a) at least one first lactam; and
   b) at least one activator for the anionic polymerization of lactams, wherein the activator comprises a compound of the formula (I)

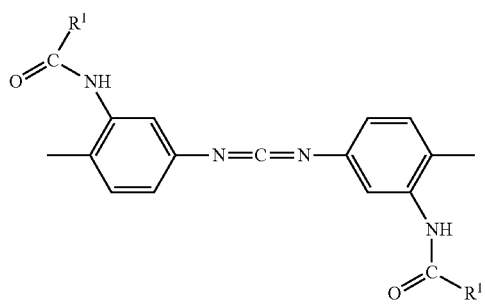

(I)

where $R^1$ is a second lactam wherein the at least one first lactam and the second lactam may be the same or different lactams.

2. The composition as claimed in claim 1, wherein the activator comprises a compound of the formula (II)

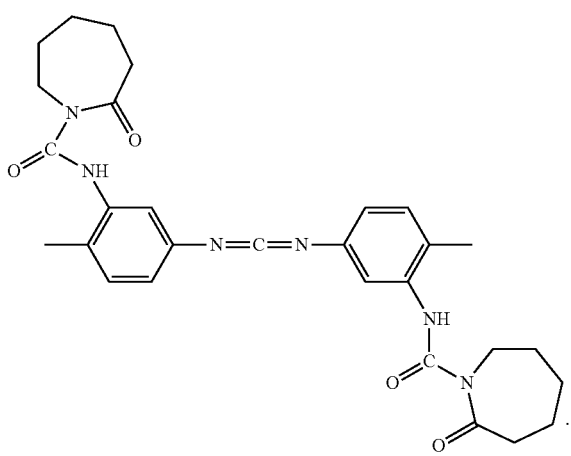

(II)

3. The composition as claimed in claim 2, wherein the at least one first lactam comprises a compound of the formula (III)

(III)

where R is an alkylene group having from 3 to 13 carbon atoms.

4. The composition as claimed in claim 2, wherein the at least one first lactam is caprolactam.

5. The composition as claimed in claim 1, wherein the at least one first lactam and the second lactam are each a compound of the formula (III)

(III)

where R is an alkylene group having from 3 to 13 carbon atoms.

6. The composition as claimed in claim 1, further comprising at least one catalyst selected from the group consisting of lactam magnesium halide, alkali-metal aluminodilactamate, alkali: metal lactamate, and alkaline-earth-metal lactamate.

7. A process for producing cast polyamides from the composition as claimed in claim 1, 2 or 6, wherein the process comprises polymerizing the constituents at temperatures of 80 to 160° C. in the form of melt.

8. A process for producing cast polyamides, the process comprising casting the composition as claimed in claim 1, 2 or 6.

9. The composition as claimed in claim 1, wherein the composition comprises:
   a) 94.2 to 99.8 wt % of the at least one first lactam,
   b) 0.2 to 0.8 wt % of the at least one activator, and
   c) 0 to 5 wt % of at least one catalyst selected from the group consisting of lactam magnesium halide, alkali-metal aluminodilactamate, alkali-metal lactamate, and alkaline-earth-metal lactamate,
   where the entirety of the constituents a) to c) is 100 wt %.

10. The composition as claimed in claim 1, wherein the at least one first lactam is at least one of: caprolactam and laurolactam.

11. A composition comprising:

a) 94.2 wt % to 99.8 wt % of at least one first lactam;

b) 0.2 wt % to 0.8 wt % of at least one activator for the anionic polymerization of lactams, wherein the activator comprises a compound of the formula (I)

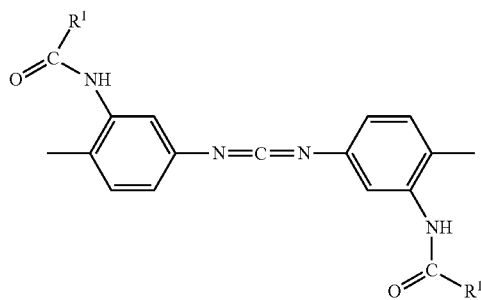

where $R^1$ is a second lactam; and c) 0 to 5 wt % of at least one catalyst for the anionic polymerization of lactams, wherein the at least one first lactam and the second lactam may be the same or different lactams where the entirety of the constituents a) to c) is 100 wt %.

12. The composition of claim 11, wherein:
the at least one first lactam is caprolactam;
the activator is a compound of the formula (II)

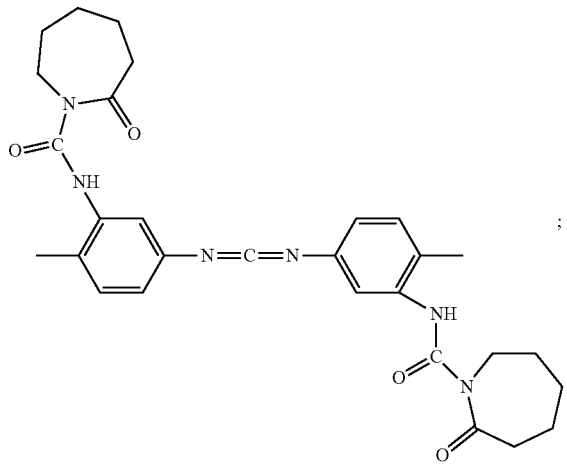

and
the composition includes an amount of the catalyst, and the catalyst is sodium caprolactamate.

* * * * *